United States Patent [19]

Terwilliger

[11] Patent Number: 4,930,515

[45] Date of Patent: Jun. 5, 1990

[54] ULTRASOUND PROBE WITH MULTI-ORIENTATION TIP-MOUNTED TRANSDUCER

[75] Inventor: Richard A. Terwilliger, San Ramon, Calif.

[73] Assignee: Diasonics, Inc., Milpitas, Calif.

[21] Appl. No.: 253,128

[22] Filed: Oct. 4, 1988

[51] Int. Cl.⁵ .............................................. A61B 8/12
[52] U.S. Cl. ............................. 128/662.06; 128/660.1; 73/633
[58] Field of Search ........................ 128/662.06, 660.1; 73/618–620, 633

[56] References Cited

U.S. PATENT DOCUMENTS 4,543,960 10/1985 Harui et al. ..................... 128/662.06
4,572,200 2/1986 Schroeder et al. ............... 128/660.1
4,756,313 7/1988 Terwilliger ................ 128/662.06 X Primary Examiner—Francis Jaworski
Attorney, Agent, or Firm—Blakely, Sokoloff, Taylor & Zafman

[57] ABSTRACT

An ultrasound probe 20 includes a transducer 32 capable of pivotal and rotational motion where the pivotal motion is through the plane of rotation. The transducer 32 is also capable of revolving around an axis of revolution 132 so that the transducer 32 can move relative to three axes. The probe 20 is designed such that the transducer 32 can be mounted at the tip of said probe 20 and allow for the above freedom of motion.

32 Claims, 9 Drawing Sheets

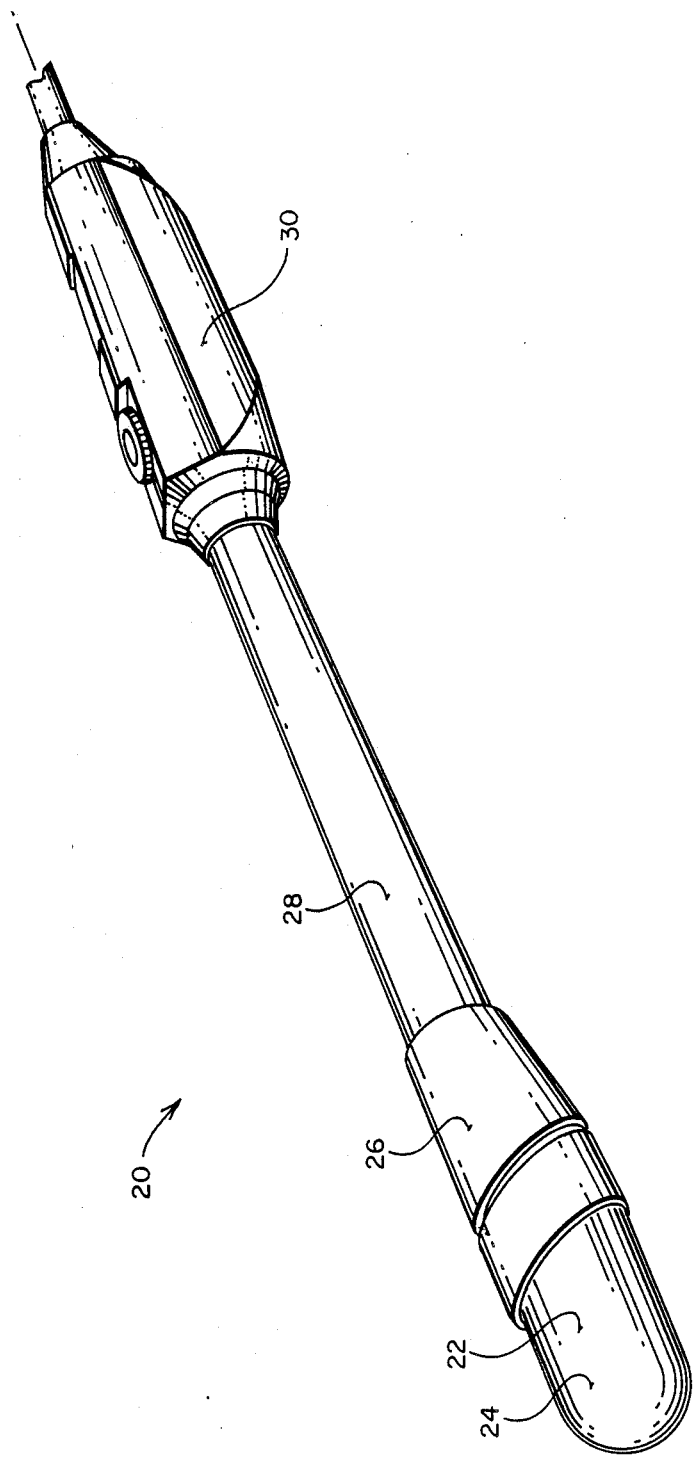
FIG—1

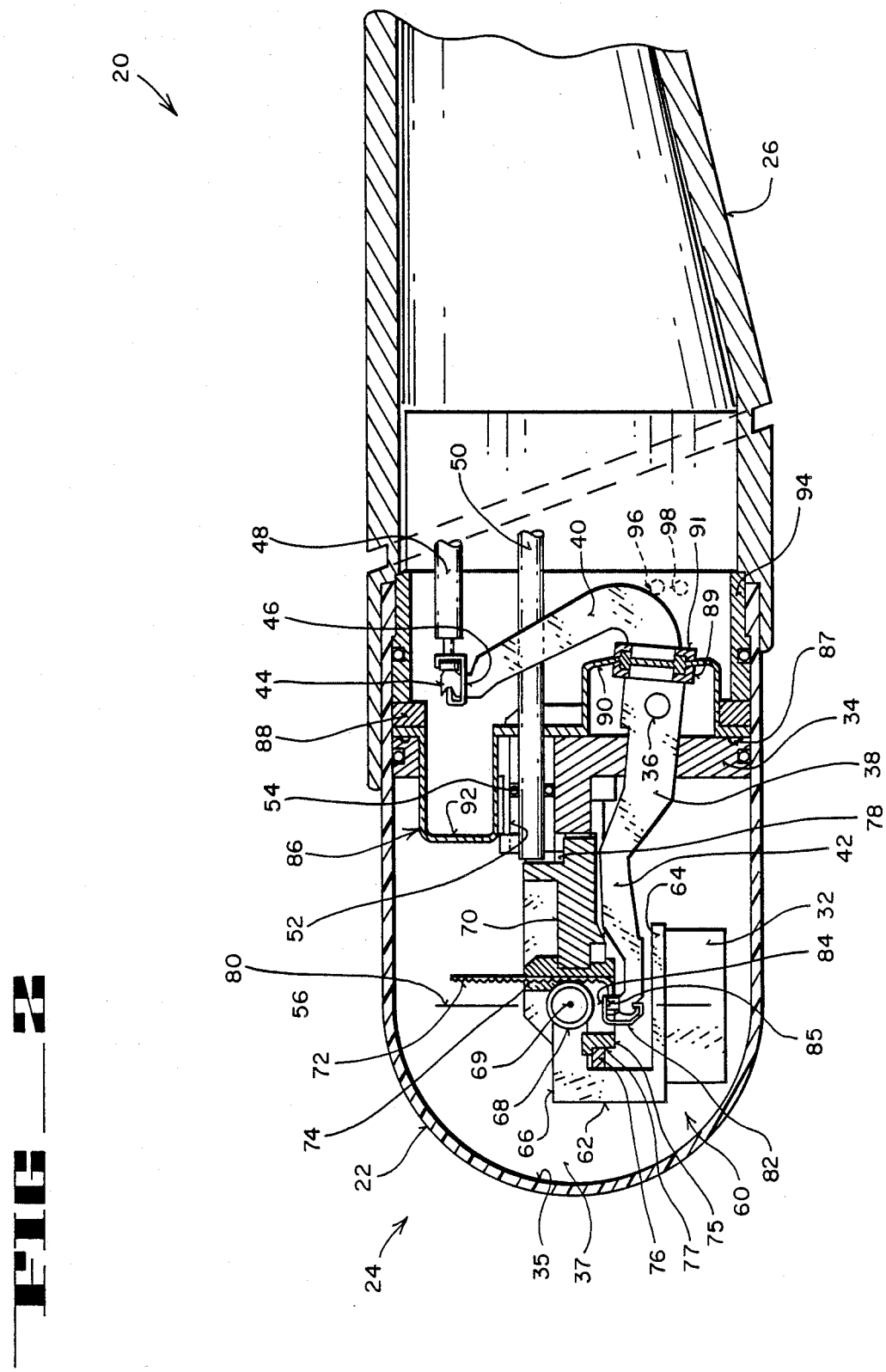

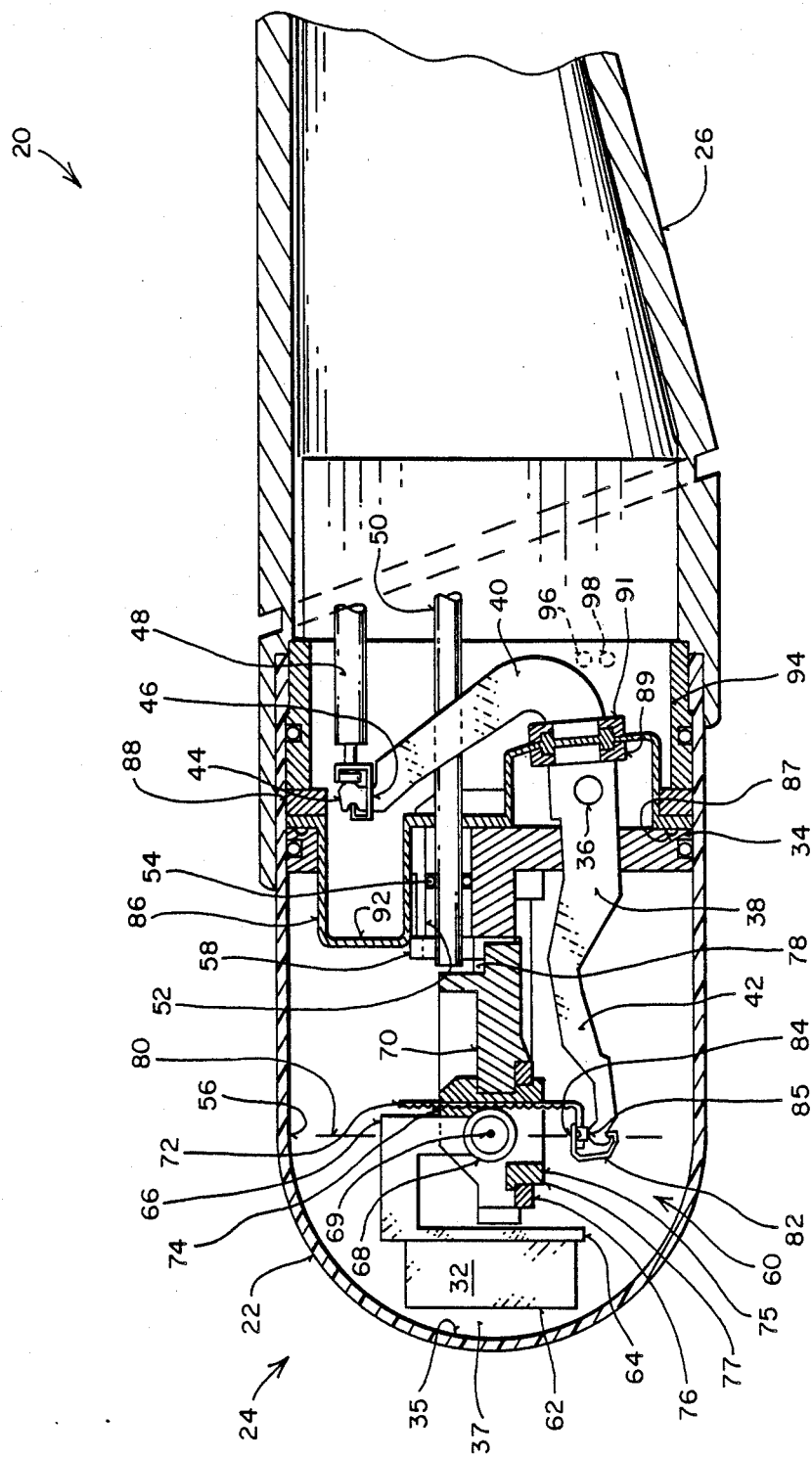
FIG_3

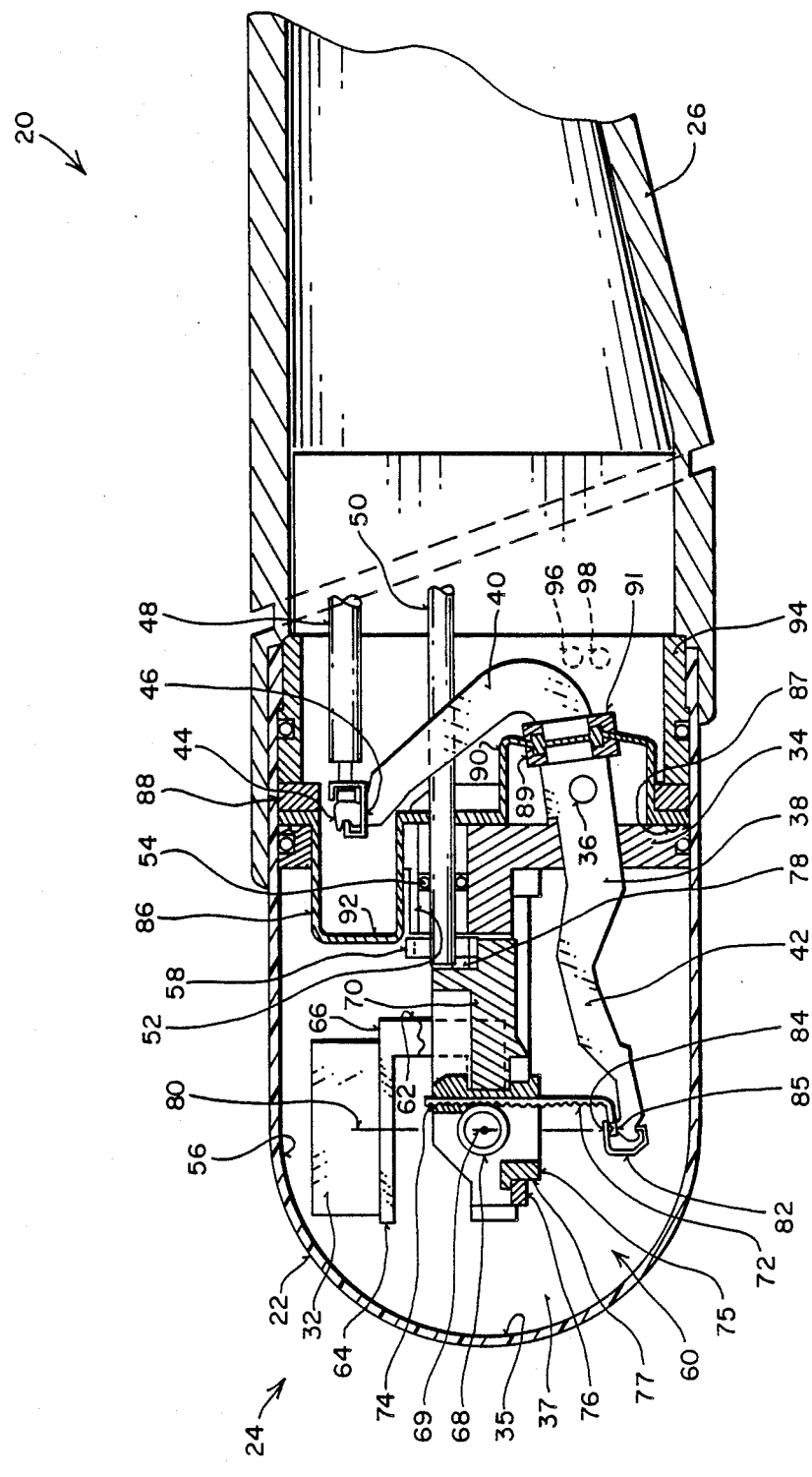
FIG_4

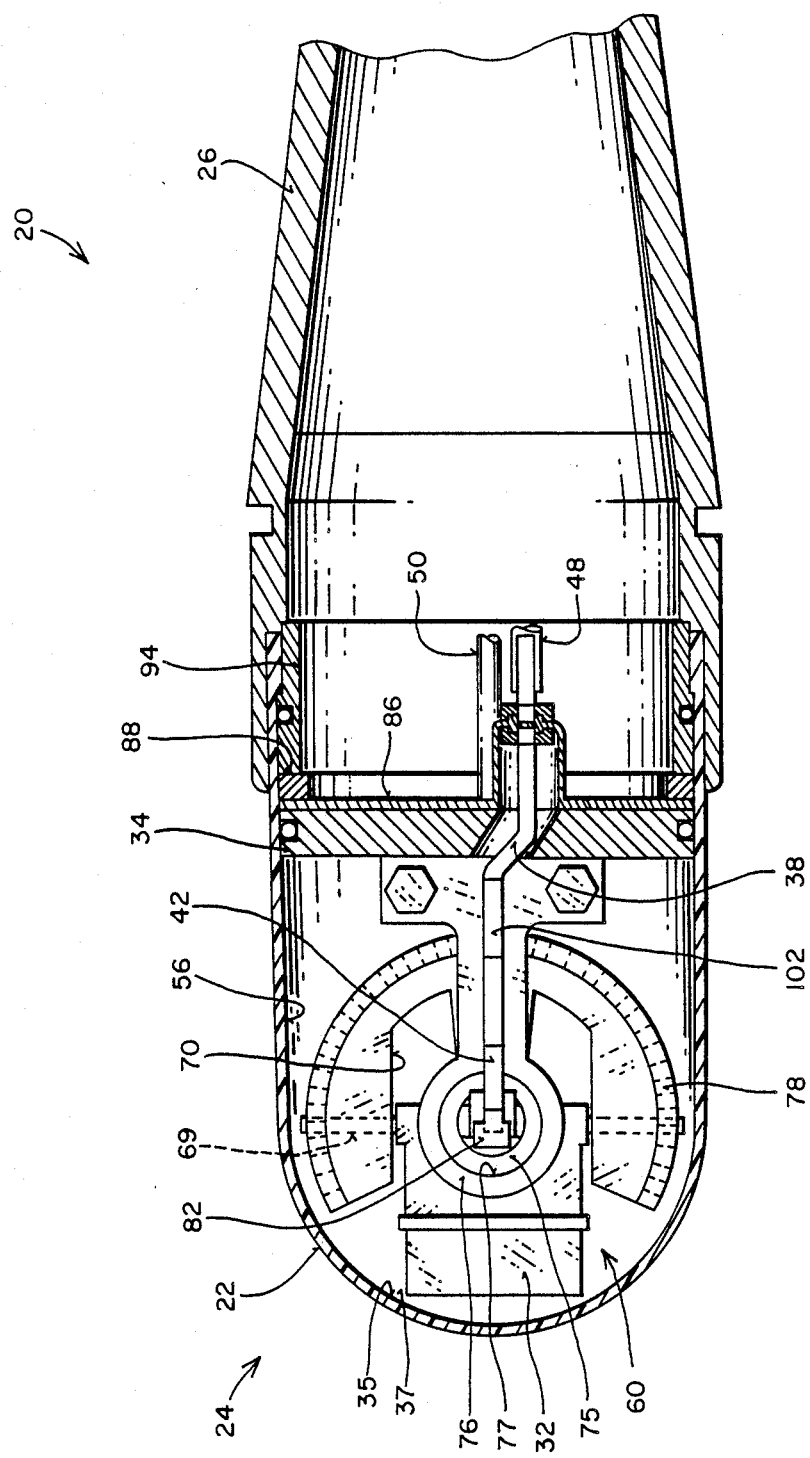

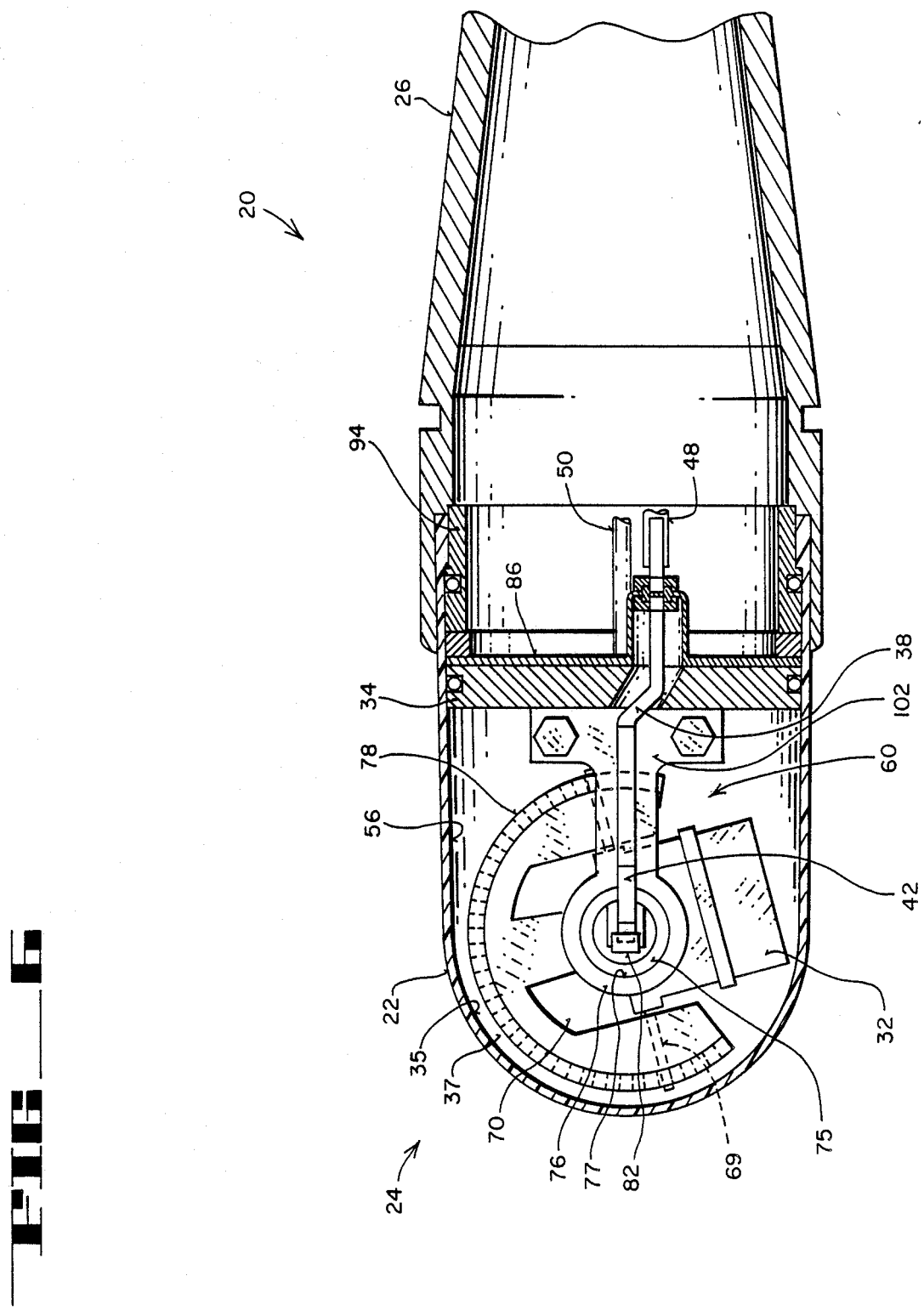
FIG_6

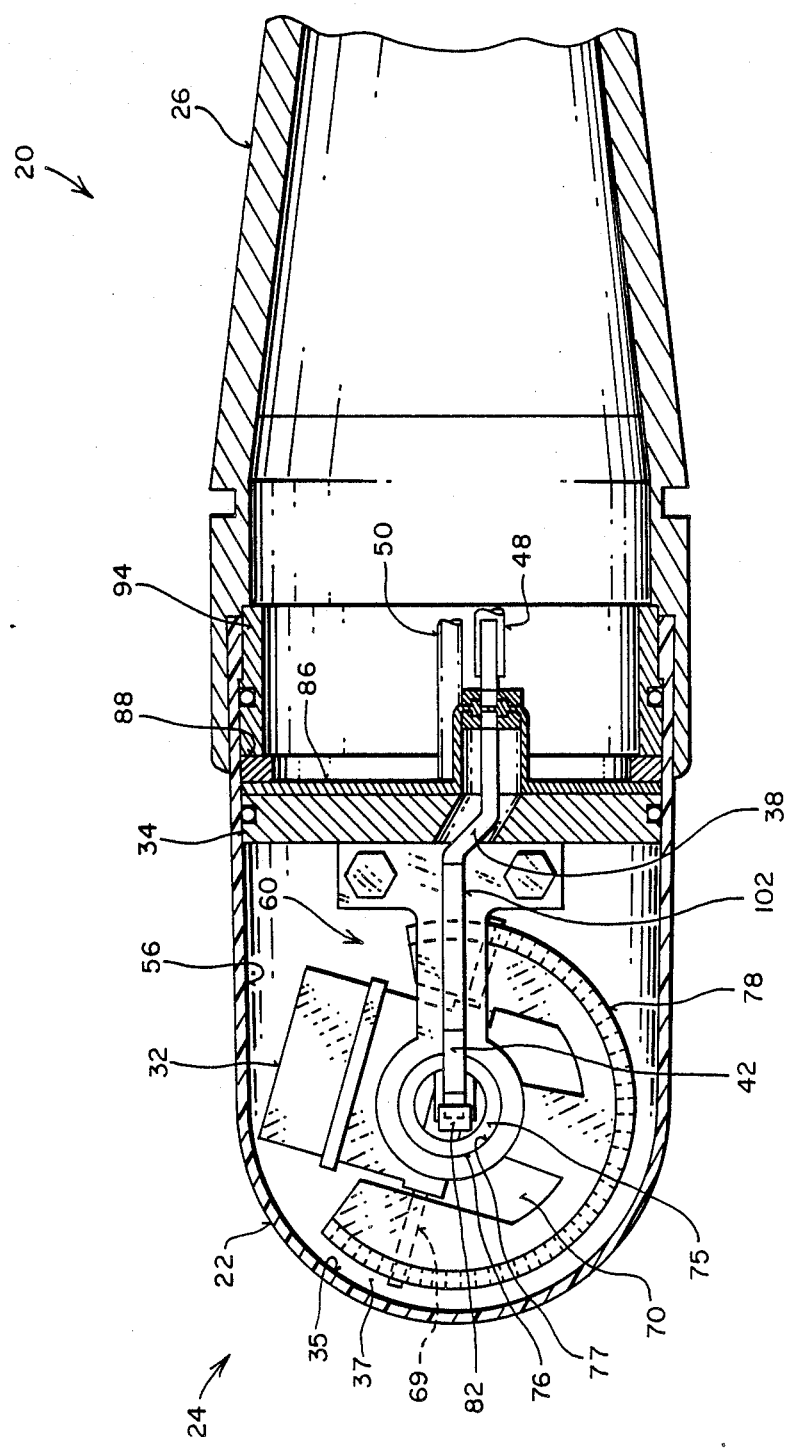
FIG.—7

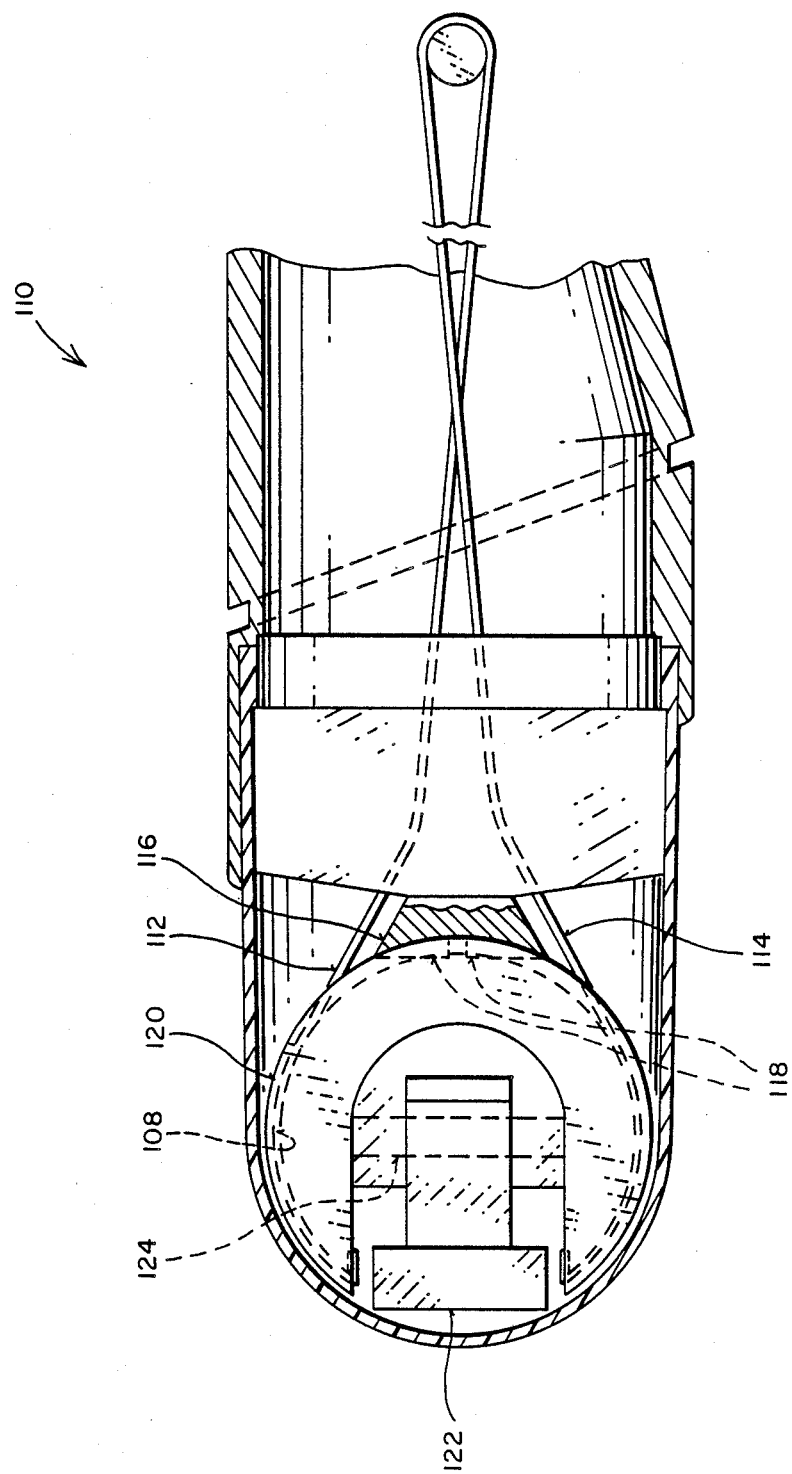
FIG—H

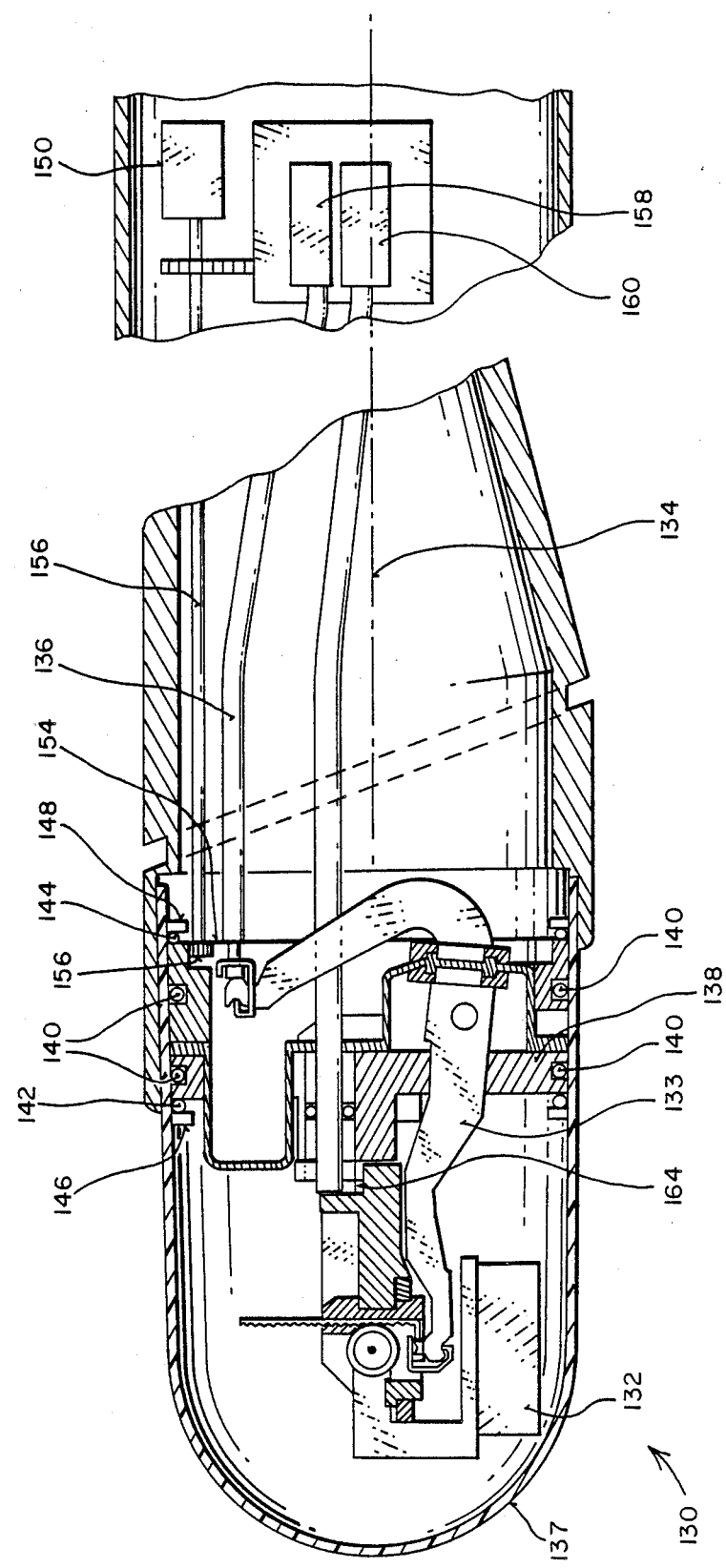
FIG__9

ULTRASOUND PROBE WITH MULTI-ORIENTATION TIP-MOUNTED TRANSDUCER

FIELD OF THE INVENTION

The present invention is directed to ultrasound probes, and in particular to ultrasound probes which are positionable in internal cavities of a subject and provide for multiple-orientation imaging.

BACKGROUND OF THE INVENTION

A number of ultrasound transducers are currently available on the market which are positionable in an internal cavity of a subject in order to make appropriate images of desired tissues. Some of these probes give the user the capability of making multiple images through the use of multiple transducers. One of the most successful ultrasound probes, however, can produce multiple images by using a single transducer which is manipulated in a unique manner. This probe is disclosed in U.S. Pat. No. 4,756,313 entitled "Ultrasonic Probe" which is assigned to DIASONICS, INC. This patent discloses an ultrasound probe with an ultrasound transducer that is provided on a mount which allows, simultaneously, for both pivotal and rotational movement. With such an ultrasound probe, high resolution images, which have heretofore been difficult to obtain at desired orientations, are readily available. The present invention is directed to improving upon the capabilities of the ultrasound probe as disclosed in the above indicated patent.

SUMMARY OF THE INVENTION

The present invention is directed towards an ultrasound probe which includes a transducer which can be caused to pivot, rotate, and revolve. Accordingly the transducer is provided with the capability of motion relative to three separate reference axes.

In an aspect of the invention, the transducer is mounted at the tip of a probe.

In another aspect of the invention, the transducer is mounted such that the transducer is allowed to pivot through a plane of rotation of the transducer.

In yet another aspect of the present invention wherein the transducer rotates about an axis of rotation, the transducer can be caused to pivot by a means which acts along the axis of rotation of said transducer.

In another aspect of the invention, the ultrasound probe is designed so that the rotational motion, as defined by a plane angle, is independent of and does not interfere with the pivotal motion, which is defined by a sector angle.

In still another aspect of the invention, a mechanism of the invention is designed in a compact manner such that, as the mechanism moves the transducer to a desired location, the mechanism can occupy space once occupied by the transducer.

In another aspect of the invention, the invention provides for a plane angle of about plus or minus 110°, with a sector angle of about plus or minus 90°.

The present invention provides for a unique clip arrangement which allows for linear motion relative to a rotating member.

In yet another aspect of the invention, rotation is accounted for using a crown gear arrangement and pivoting is accounted for using a rack and pinion arrangement.

In another aspect of the invention, wherein pivoting is accounted for using a rack and pinion arrangement, the rack operates through the axis of rotation of the mechanism which causes the transducer to pivot.

In another aspect of the invention, a seal is provided to allow motion to be passed through to a chamber containing the transducer and ultrasound transmitting fluid. The seal is provided so that it can collapse in order to account for transducer fluid pressure differences caused by temperature changes in the probe.

BRIEF DESCRIPTION OF THE FIGURES

FIG. 1 is a perspective view of an embodiment of an ultrasound probe in accordance with the present invention.

FIG. 2 is a cut-away side view of the embodiment of FIG. 1 with a transducer having a plus 90° sector angle and a 0° plane angle.

FIG. 3 is a cut-away side view of an embodiment of the present invention similar to FIG. 2 but with the transducer having a 0° sector angle and 0° plane angle.

FIG. 4 is a cut-away side view similar to FIG. 2 with the transducer having a minus 90° sector angle and a 0° plane angle.

FIG. 5 is a cut-away side view of an embodiment of the present invention along line 5—5 in FIG. 3.

FIG. 6 is a cut-away side view similar to FIG. 5 but with the transducer having a plane angle of 110° and a sector angle of about 0°.

FIG. 7 is a cut-away side view similar to FIG. 5 but with the transducer having a plane angle of minus 110° and a sector angle of 0°.

FIG. 8 is a cut-away side view of another embodiment of the present invention whereby rotation is accounted for with a pulley mechanism.

FIG. 9 is a cut-away side view of yet another embodiment of the present invention which allows for transducer movement relative to three axes.

DETAILED DESCRIPTION OF THE PREFERRED EMBODIMENTS

With references to the Figures and in particular to FIG. 1, an ultrasound probe 20 of the present invention is depicted. The ultrasound probe 20 includes a membrane 22 located at a distal or tip end 24 of the probe 20. The membrane 22 provides an enclosure about an ultrasound transducer and contains ultrasound fluid which surrounds the ultrasound transducer. A membrane clamp cover 26 is located immediately behind the membrane 22 and provides a transition between the membrane 22 and the elongate probe shaft 28. Secured to the other end of the probe shaft 28 is the probe handle 30.

Viewing FIG. 2, probe 20 is depicted with a transducer 32 positioned with a plus 90° sector angle and a 0° plane angle.

The ultrasound probe 20 includes a bulk head 34 having a pivot shaft 36 mounted thereto. The bulkhead 34 and the membrane 22 enclose a chamber 35 which contains ultrasound transmitting fluid 37. Pivotally mounted to the pivot shaft 36 is a substantially L-shaped lever 38. Lever 38 includes a lower leg 40 and an upper leg 42. The upper leg 42 is positioned inside chamber 35 substantially adjacent to the transducer 32 with the lower leg 40 positioned on the other side of the bulkhead 34 from the transducer 32. The lower leg 40 at an end 44 thereof, is provided with a clip 46 which allows a piston 48 to be secured thereto. The piston 48 provides driving motion from, in a preferred embodiment, a linear motor (not shown). The clip 46 allows for a dynamic connection between the piston 48 and the lower leg 40 so that the linear motor can cause the lever 38 to pivot about the pivot shaft 36.

Also projecting through the bulkhead 34 is a rotational drive shaft 50 which is mounted in a bore 52 provided through bulkhead 34. Appropriate sealing O-rings such as O-ring 54 are provided in order to containing the ultrasound fluid 37. At the end of rotational drive shaft 50 is a gear 58 for causing rotation of the transducer 32.

Transducer 32 is mounted to a transducer mounting block 60 as can be seen in FIG. 2. Transducer mounting block 60 is substantially U-shaped and includes a base 62, a first-leg portion 64, and a second leg portion 66. The transducer 32 is secured to the first leg portion 64. The second leg portion 66 includes a pinion gear 68.

The transducer mounting block 60 is pivotally mounted to rotational frame 70 such that block 60 can pivot above pivot axis 69. Also mounted to rotational frame 70 is a rack 72 which is positioned in a retaining channel 74 of rotational frame 70. Rack 72 engages the pinion gear 68 in order to pivot the transducer mounting block 60 and thus the transducer 32 as will be discussed hereinbelow.

Rotational frame 70 is rotatably mounted upon a plate 76, which plate 76 is secured to the bulkhead 34. This mounting is accomplished with a cylindrical extension 75 of frame 70 which snaps into an aperture 77 of plate 76. Rotational frame 70 is substantially circular in configuration and further includes at its outer periphery a crown gear 78. Crown gear 78 meshes with the gear 58 mounted on the rotational drive shaft 50 in order to cause the crown gear 78 and the rotational frame 70 to rotate about an axis of rotation 80 which is co-linear with the longitudinal axis of rack 72.

A clip 82 is used to operably secure the lever 38 to the rack 72 so that the lever 38 can operate the rack 72 as the rack 72 is rotating. To accomplish this, the clip includes a conically shaped point of rotation 84 which engages a conically shaped indentation 85 in the rack 72 to allow the rack 72 to rotate relative to the clip 82 and the lever 38.

A seal 86 is provided in order to seal the ultrasound fluid 37 contained within the membrane 22 from the remainder of the probe 20. This seal 86 is located behind the bulkhead 34 and retained in place in sealing engagement with the bulkhead 34 by a nut plate 88. Seal 86 is comprised of flexible rubber materials known in the trade and includes first and second cavities 90 and 92. The first cavity 90 is provided about the pivot shaft 36 for the lever 38. Second cavity 92 is positioned to receive the end 44 of the lever 38 at an end drive position of piston 48.

Additionally, seal 86 allows for temperature compensation by allowing the first and second cavities 90, 92 to collapse in order to maintain the pressure within the membrane 22. Temperature variations can occur when, for example, the probe 20 is taken from storage and placed in a cavity of a subject. As probe 20 warms, there is an increase in pressure inside membrane 22. When this occurs, the second cavity 92 collapses to relieve the pressure increase. When the probe 30 is removed from the cavity in the subject and again stored, the temperature and pressure are reduced. As this occurs the first cavity 90 can collapse in to maintain a constant pressure. Thus the operation of the invention and the positioning of the trafisducer is not slowed down or in any way affected by temperature variation or pressure variations.

The seal 86 includes beads, such as bead 87, which are compressible between bulkhead 34 and nut plate 88 for providing an airtight seal. Further snap caps 89 and 91 are provided for providing a seal between the lever 38 and seal 86.

Located immediately behind the nut plate 88 is a fill port block 94 which includes ports 96 and 98. Port 96 allows ultrasound fluid to be poured into the chamber 35 defined by membrane 22, while port 98 allows air to escape as the filling operation proceeds. Appropriate plugs are placed over the ports when the filling operation is completed.

FIGS. 2 through 7 demonstrate how the transducer 32 can be selectively positioned inside of the ultrasound probe 20. In FIG. 2, the transducer 32 is shown in a position with a plane angle of 0° (orientation of the rotational frame 70) and a sector angle of 90° (pivotal position of the transducer mounting block 60). In this configuration, it is noted that the rack 72 is urged along the axis of rotation 80 and extends through the plane of the rotational frame 70, on the opposite side of the rotation frame 70 from the transducer 32. In fact the rack 72 occupies a space which will eventually be occupied by the transducer 32 when it is moved to another position. It is noted that the transducer mounting block 60 wraps around the upper leg 42 of the lever 38 where the upper leg 42 is secured by the clip 82 to the rack 72. The upper leg 42 is received in a slot 102 (FIG. 5) defined in the plate 76 which retains the rotational frame 70. The lower leg 40 is shown at its furthest position from seal 86.

In FIG. 3, the transducer 32 is positioned such that the plane angle is 0 and the sector angle is 0. Comparing FIGS. 2 and 3 it can be seen that the transducer 32 is moving through the plane of rotation which is defined by the rotational frame 70, with the rack 72 also moving through the plane of rotation along the axis of rotation 80 of the rotational frame 70. The rack 72 is being pulled to a position which has been vacated by the transducer 32, the rack 72 accordingly being removed from the position to which the transducer 32 is moving. It is also noted that the lower leg 40 is being urged by the piston towards the cavity 92 of seal 86.

In FIG. 4, the transducer is shown in a position such that the plane angle is 0° with the sector angle being negative 90°. In this position it can be seen that the rack 72 and upper leg 42 have fully occupied the space previously occupied by the transducer 32 and the transducer 32 has been positioned in the space previously occupied by the rack 72. The transducer 32 has been pivoted through the plane of rotation of frame 70 with the rack 72 fully extended on the other side of the rotational frame 70 along the axis of rotation 80. The lower leg 42 has been urged to a position which is adjacent the bulkhead 34 and partially received by the second cavity 92.

Viewing FIG. 5, the transducer 32 is shown in a similar configuration to that of FIG. 3 but along a different plane so that the rotationaly frame 70 is shown with its axis of rotation perpendicular to the page.

FIG. 6 demonstrates the transducer 32 position with a plane angle of 110° and a sector angle of 0°. FIG. 7 demonstrates a plane angle of negative 110° and a sector angle of 0°. In these figures it can be seen that the upper leg 42 can be received in the slot 102 defined by the plate 76 which rotatably mounts the rotational frame 70.

An alternate embodiment of the invention is shown in FIG. 8. In this embodiment, the rotational frame 108 is caused to rotate by a pulley arrangement 110 which includes pulley wires 112 and 114 which are secured to the rotational frame 108 in order to cause it to rotate relative to base 116. Rotational frame 108 is held against base 116 by the pulley wires 112, 114. Extending from the base 116 are pins 118 which are received in a groove 120 of the rotational frame 108 in order to guide the rotational movement of the frame 108. The transducer 122 is allowed to pivot about pivotal axis 124. This embodiment allows the transducer 122 to have all the freedom of operation as shown in the first embodiment in FIGS. 1 through 7.

A further embodiment 130 of the invention is shown in FIG. 9. In this embodiment, the transducer 132 is not only allowed to pivot and rotate as in the embodiments shown in the previous figures but is also allowed to revolve about an axis of revolution 134. Thus the transducer 132 can move relative to three axes which can if desired be perpendicular to each other. Pivotal motion which is transferred to lever 133 is transferred along a flexible drive shaft 136. The bulkhead 138 is mounted for revolution relative to the membrane 137, on ball bearings 140 such that the transducer 132 can revolve plus or minus 180 degrees about the axis of revolution 134. "O-rings" 142, 144 provide a seal between the bulkhead 138 and annular guides 146, 148. The revolution of the bulkhead 138 is accomplished through a motor 150 and drive shaft 152. A gear 154 at the end of shaft 152 engages a gear 156 which is formed in bulkhead 138 in order to cause the bulkhead 138 and thus the transducer 132 to revolve. Motors 158 and 160 which actuate lever 133 and crown gear 164 respectively, are also caused to revolve by motor 150.

INDUSTRIAL APPLICABILITY

The operation of the ultrasound probe 20 of the invention is as follows. The ultrasound probe 20 can be positioned in the appropriate cavity of a subject. Then transducer 32 can be caused to pivot through sector angles of plus or minus 90° and rotate through plane angles of plus or minus 110° in a preferred embodiment. Further the transducer 32 can be caused to revolve through revolution angles of plus or minus 180° in preferred embodiment. In other embodiments the sector angles, the plane angles, and the revolution angles can be selected as desired. Such motions can be accomplished in a preferred embodiment along three mutually perpendicular axes and thus give the ultrasound probe 20 substantial flexibility in imaging desired tissue.

It is to be understood that such flexibility is accomplished due to the fact that the transducer 32 can pivot through the plane of rotation. Further the mechanism which accounts for the pivoting acts colinear with the axis of rotation. The ultrasound probe 20 is designed in a compact manner such that the mechanism which causes the transducer 32 to pivot, itself moves to occupy space previously occupied by the transducer 32. Further the probe 20 advantageously provides for a seal which allows for temperature and pressure compensation such that increased pressure due to the increased temperature is relieved and thus does not affect the operation of the probe.

Other objects and aspects of the invention can be obtained from a review of the claims and figures.

It is to be understood that other embodiments of the invention can be provided which fall within the spirit and scope of the claims.

We claim:

1. A probe comprising:
   a probe housing;
   a transducer capable of at least one of sending and receiving a signal;
   means for pivotally mounting said transducer;
   means for pivoting said transducer so that the signal of the transducer describes a signal plane relative to the lengthwise axis of said probe housing as the transducer pivots lengthwise;
   means for rotationally mounting said pivotally mounting means so as to describe a plane of rotation perpendicular to said signal plane and relative to the lengthwise axis of said probe housing;
   wherein said pivotally mounting means includes means for allowing said transducer to be pivoted through said plane of rotation;
   means for operably connecting said transducer pivoting means to said pivotally mounting means;
   means for rotating said rotationally mounting means and said pivotally mounting means while said transducer pivoting means pivots said transducer, such that said signal plane described by the pivoting transducer rotates.

2. The probe of claim 1 wherein said transducer is an ultrasound transducer.

3. The probe of claim 1 including:
   means for causing said pivotally mounting means and said rotationally mounting means to revolve about an axis of revolution.

4. The probe of claim 1 wherein said operably connecting means includes:
   a rack;
   means for mounting said rack on said rotationally mounting means;
   a pinion;
   means for incorporating said pinion with said pivotally mounting means.

5. The probe of claim 4 wherein:
   said rotationally mounting means defines an axis of rotation for said transducer; and
   wherein said operably connecting means includes means for moving said rack along said axis of rotation.

6. The probe of claim 1 wherein:
   said pivotally mounting means includes means for receiving part of said operably connecting means as said transducer is pivoted in to an operably connecting means receiving position in order to increase the freedom of pivotal motion of said pivotally mounting means.

7. The probe of claim 1 wherein:
   said pivotally mounting means includes first means for receiving part of said operably connected means with the transducer in a first position and second means for receiving part of said rotationally mounting means with said transducer in a second position rotated from the first position in order to increase the freedom of pivotal motion of said pivotally mounting means.

8. The probe of claim 1 wherein:
   said operably connecting means includes:
   (a) a rack;
   (b) means for mounting said rack on said rotationally mounting means;

(c) a pinion;
(d) means for incorporating said pinion with said pivotally mounting means;
(e) a lever;
(f) means for operably connecting said lever to said rack;
wherein said rotationally mounting means defines an axis of rotation for said transducer;
wherein said rack is moved along said axis of rotation by said lever;
wherein said rotationally mounting means has first and second sides, with said rack movable along said axis of rotation in order to project selectively and more predominant from one of said first and second sides; and
said pivotally mounting means includes (a) first means for receiving part of said levers and said rack with said pivotally mounting means located adjacent said first side of said rotationally mounting means and said rack projecting from said second side, and (b) second means for receiving part of said rotationally mounting means with said transducer pivotal to a position adjacent to said second side and with the rack extending from the first side and at least substantially retracted from the second side.

9. The probe of claim 1 including:
means for containing ultrasound transmitting fluid surrounding said transducer; and
collapsible means for compensating for pressure changes in the ultrasound transmitting fluid due to temperature changes.

10. The probe of claim 1 wherein said operably connecting means includes:
a rack;
means for mounting said rack on said rotationally mounting means;
a pinion;
means for incorporating said pinion with said pivotally mounting means;
a lever;
clip means for operably connecting said lever to said rack to allow said rack to rotate with said transducer.

11. A probe comprising:
a probe housing;
a transducer capable of at least one of sending and receiving a signal;
means of pivotally and rotationally mounting said transducer;
means for operably connecting said pivoting means to said mounting means for pivoting said transducer so that said signal of said transducer describes a signal plane relative to the lengthwise axis of said probe housing as the transducer pivots;
means for rotating said transducer while said pivoting means pivots said transducer having a plane of rotation perpendicular to said signal plane being described by said rotating means;
means for operably connecting said rotating means to said mounting means, such that said signal plane described by the pivoting transducer can be caused to rotate;
wherein said mounting means includes means for allowing said transducer to be pivoted through said plane of rotation.

12. The probe of claim 11 wherein said transducer is an ultrasound transducer.

13. The probe of claim 11 including:
means for causing said pivotally and rotationally mounting means to revolve about an axis of revolution.

14. The probe of claim 11 wherein said operably connecting means includes:
a rack;
means for mounting said rack on said pivotally and rotationally mounting means;
a pinion;
means for incorporating said pinion with said pivotally mounting means;
wherein said pivotally and rotationally mounting means defines an axis of rotation for said transducer; and
wherein said operably connecting means includes means for moving said rack along said axis of rotation.

15. The probe of claim 11 wherein:
said pivotally and rotationally mounting means includes means for receiving part of said operably connecting means as said transducer is pivoted in to an operably connecting means receiving position in order to increase the freedom of pivotal motion of said pivotally and rotationally mounting means.

16. The probe of claim 11 wherein:
said pivotally and rotationally mounting means includes first means for receiving part of said operably connected means with the transducer in a first position and second means for receiving part of said rotationally mounting means with said transducer in a second position rotated from the first position in order to increase the freedom of pivotal motion of said pivotally and rotationally mounting means.

17. The probe of claim 11 including:
means for containing ultrasound transmitting fluid surrounding said transducer; and
means for compensating for pressure changes in the ultrasound transmitting fluid due to temperature changes.

18. The probe of claim 17 wherein said compensating means include a collapsible cavity.

19. An elongate probe capable of at least one of sending and receiving a signal comprising:
an elongate housing having an elongate side surface and a first end;
a transducer capable of at least one of sending and receiving a signal;
means for pivotally mounting said transducer relative to said housing at said first end such that said signal describes a signal plane that is substantially parallel to said elongate side surface;
means for rotationally mounting said pivotally mounting means with a plane of rotation being described;
means for pivoting said transducer so that the signal of the transducer describes said signal plane as the transducer pivots, such that said pivotally mounting means includes means for allowing said transducer to be pivoted through said plane of rotation;
means for operably connecting said transducer pivoting means to said pivotally mounting means;
means for rotating said pivotally mounting means while said transducer pivoting means pivots said transducer, such that said transducer rotates, and such that said signal plane described by the pivoting transducer is rotated.

20. The probe of claim 19 wherein:
said transducer is an ultrasound transducer.

21. The probe of claim 19 including:
means for causing said pivotally mounting means and said rotationally mounting means to revolve about an axis of revolution.

22. An elongate probe capable of at least one of sending and receiving a signal comprising:
an elongate housing having an elongate side surface and a first end;
a transducer capable of at least one of sending and receiving a signal;
means for mounting said transducer at said first end;
first means for moving said transducer mounting means such that said signal transducer describes a signal plane relative to said elongate probe;
second means for moving said transducer mounting means such that the signal plane rotates about an axis of rotation located in said signal plane; and
wherein said first moving means includes means for allowing said transducer to move through said plane of rotation which is perpendicular to said axis of rotation.

23. The probe of claim 22 wherein said transducer is an ultrasound transducer.

24. The probe of claim 22 including:
means for causing said transducer mounting means to revolve about an axis of revolution.

25. A probe comprising:
a probe housing;
a transducer capable of at least one of sending and receiving a signal;
means for pivotally mounting said transducer relative to said housing;
means for rotationally mounting said pivotally mounting means to said housing such that said pivotally mounting means rotates about an axis of rotation relative to said probe housing;
means for pivoting said transducer such that said signal of said transducer describes a signal plane as said transducer pivots, said pivoting means including means for acting along said axis of rotation to cause said pivotally mounting means to pivot;
means operably connecting said transducer pivoting means to said pivotally mounting means;
means for rotating said rotationally mounting means, and said pivotally mounting means while said transducer pivoting means pivots said transducer, such that said signal plane described by said pivoting transducer is rotated.

26. The probe of claim 25 including:
means for causing said pivotally mounting means and said rotationally mounting means to revolve about an axis of revolution.

27. A probe comprising:
a probe housing;
a transducer capable of at least one of sending and receiving a signal;
means for pivotally and rotationally mounting said transducer;
means for pivoting said transducer;
means for operably connecting said pivoting means to said mounting means for pivoting said transducer such that said signal of said transducer describes a signal plane as said transducer pivots;
means for rotating said transducer while said pivoting means pivots said transducer;
means for operably connecting said rotating means to said mounting means, such that said signal plane described by said pivoting transducer rotates about an axis of rotation;
wherein said pivoting means includes means for acting along said axis of rotation to cause said mounting means to pivot.

28. The probe of claim 27 including:
means for causing said pivotally and rotationally mounting means to revolve about an axis of revolution.

29. An elongate probe capable of at least one of sending and receiving a signal comprising:
an elongate housing having an elongate side surface and a first end;
a transducer capable of at least one of sending and receiving a signal;
means for pivotally mounting said transducer relative to said housing at said end first such that said signal describes a signal plane that is substantially parallel to said elongate side surface;
means for rotationally mounting said pivotally mounting means about an axis of rotation wherein a plane of rotation is described;
means for pivoting said transducer such that said signal of said transducer describes said signal plane as said transducer pivots;
means operably connecting said transducer pivoting means to said pivotally mounting means;
means for rotating said pivotally mounting means while said transducer pivoting means pivots said transducer, such that said transducer rotates, and such that said signal plane described by said pivoting transducer rotates; and
wherein said pivotally mounting means includes means for acting along said axis of rotation to cause said mounting means to pivot.

30. The probe of claim 29 including:
means for causing said pivotally mounting means and said rotationally mounting means to revolve about an axis of revolution.

31. An elongate probe capable of at least one of sending and receiving a signal comprising:
an elongate housing having an elongate side surface and a first end;
a transducer capable of at least one of sending and receiving a signal;
means for mounting said transducer at said first end;
first means for moving said transducer mounting means such that said signal transducer describes a signal plane;
second means for moving said transducer mounting means such that said signal plane rotates about an axis of rotation located in said signal plane; and
wherein said first means includes means for acting along said axis of rotation to cause said signal transducer to describe said signal plane.

32. The probe of claim 31 including:
means for causing said transducer mounting means to revolve about an axis of revolution.

* * * * *

UNITED STATES PATENT AND TRADEMARK OFFICE
CERTIFICATE OF CORRECTION

PATENT NO. : 4,930,515
DATED : June 5, 1990
INVENTOR(S) : Richard A. Terwilliger It is certified that error appears in the above-indentified patent and that said Letters Patent is hereby corrected as shown below:

Column 3, line 63, delete "30", insert --20--.

Signed and Sealed this

Twenty-sixth Day of December, 1995

Attest:

BRUCE LEHMAN

*Attesting Officer*     *Commissioner of Patents and Trademarks*